(12) United States Patent
Hathorn

(10) Patent No.: US 11,701,286 B2
(45) Date of Patent: Jul. 18, 2023

(54) ENDOSCOPY BAND WITH SIGMOID SUPPORT APPARATUS

(71) Applicant: ColoWrap, LLC, Durham, NC (US)

(72) Inventor: James Hathorn, Durham, NC (US)

(73) Assignee: ColoWrap, LLC, Durham, NC (US)

( * ) Notice: Subject to any disclaimer, the term of this patent is extended or adjusted under 35 U.S.C. 154(b) by 314 days.

(21) Appl. No.: 16/818,877

(22) Filed: Mar. 13, 2020

(65) Prior Publication Data

US 2020/0206058 A1   Jul. 2, 2020

Related U.S. Application Data

(63) Continuation of application No. 15/256,019, filed on Sep. 2, 2016, now Pat. No. 10,624,808, which is a (Continued)

(51) Int. Cl.
*A61F 5/00*   (2006.01)
*A61B 17/00*   (2006.01)
(Continued)

(52) U.S. Cl.
CPC ............ *A61H 1/008* (2013.01); *A61B 90/17* (2016.02); *A61F 5/0009* (2013.01); *A61F 5/03* (2013.01); *A61F 5/30* (2013.01); *A61F 13/148* (2013.01); *A61B 2017/00818* (2013.01); *A61F 5/26* (2013.01); *A61H 2205/083* (2013.01)

(58) Field of Classification Search
CPC .. A61F 5/03; A61F 5/0009; A61F 5/26; A61F 5/30; A61F 13/148; A61H 1/008; A61B 90/17

See application file for complete search history.

(56) References Cited

U.S. PATENT DOCUMENTS 3,115,879 A   12/1963   Kaplan
3,120,846 A   2/1964   Fletcher
(Continued)

FOREIGN PATENT DOCUMENTS

CN   202161367 U   3/2012
GB   2 381 732 A   5/2003
(Continued)

OTHER PUBLICATIONS

European Search Report of related European Patent Application No. 12864172.7 dated Sep. 2, 2015.
(Continued)

*Primary Examiner* — Diane D Yabut
(74) *Attorney, Agent, or Firm* — Procopio, Cory, Hargreaves & Savitch LLP

(57) ABSTRACT

An endoscopy sigmoid support apparatus that includes a primary wrap sized for placement around a subject's lower abdomen. A closing mechanism is provided at the end of the primary wrap to secure the primary wrap around the abdomen of the subject by attaching a first end of the primary wrap to a second portion of the primary wrap. A strap extends from the primary wrap and is configured to extend across at least a portion of the primary wrap and to fasten to a third portion of the primary wrap to adjust the amount of pressure applied by the endoscopy sigmoid support apparatus.

20 Claims, 26 Drawing Sheets

Related U.S. Application Data continuation-in-part of application No. 14/575,860, filed on Dec. 18, 2014, now Pat. No. 10,441,222, said application No. 15/256,019 is a continuation-in-part of application No. 13/344,715, filed on Jan. 6, 2012, now Pat. No. 9,724,225.

(60) Provisional application No. 62/214,747, filed on Sep. 4, 2015, provisional application No. 61/944,658, filed on Feb. 26, 2014, provisional application No. 61/917,469, filed on Dec. 18, 2013.

(51) Int. Cl.
  *A61H 1/00* (2006.01)
  *A61F 5/30* (2006.01)
  *A61B 90/17* (2016.01)
  *A61F 13/14* (2006.01)
  *A61F 5/03* (2006.01)
  *A61F 5/26* (2006.01)

(56) References Cited

U.S. PATENT DOCUMENTS

| | | |
|---|---|---|
| 3,554,190 A | 1/1971 | Kaplan |
| 3,902,503 A | 9/1975 | Gaylord, Jr. |
| 4,833,730 A | 3/1989 | Nelson |
| 4,991,234 A | 2/1991 | Greenberg |
| 5,188,585 A | 2/1993 | Peters |
| 5,489,260 A | 2/1996 | Striano |
| 5,647,824 A | 7/1997 | Levenson |
| 5,685,321 A | 11/1997 | Klingenstein |
| 5,820,575 A | 10/1998 | Cabrera et al. |
| 5,885,230 A | 3/1999 | Cherry |
| 6,672,311 B2 | 1/2004 | Rindfleish |
| 8,066,657 B2 | 11/2011 | Frazer |
| 2002/0108617 A1 | 8/2002 | Burton |
| 2011/0087263 A1 | 4/2011 | Arber |
| 2013/0110019 A1* | 5/2013 | Hopman ............... A61F 5/34 602/19 |
| 2013/0178893 A1 | 7/2013 | Hathorn |
| 2014/0323802 A1 | 10/2014 | Lloyd |

FOREIGN PATENT DOCUMENTS

| | | |
|---|---|---|
| JP | 3051938 U | 6/1998 |
| JP | 2005-021113 A | 1/2005 |
| JP | 2006-314711 A | 11/2006 |
| KR | 200264387 Y1 | 2/2002 |
| WO | WO 9508308 A1 | 3/1995 |
| WO | WO 9614811 A1 | 5/1996 |
| WO | WO 9746180 A1 | 12/1997 |

OTHER PUBLICATIONS

International Search Report and Written Opinion of related International Patent Application No. PCT/US2014/071218 dated Mar. 24, 2015.

Soper, Nathaniel J., et al., "Chapter 45: Flexible Endoscopy of the Lower Gastrointestinal Tract, Endoscopic and Laparoscopic Surgery," Lippincott Williams & Wilkins, Philadelphia, PA, 2009, pp. 451.

* cited by examiner

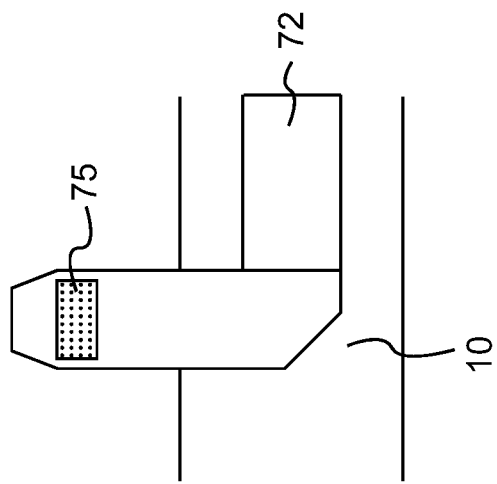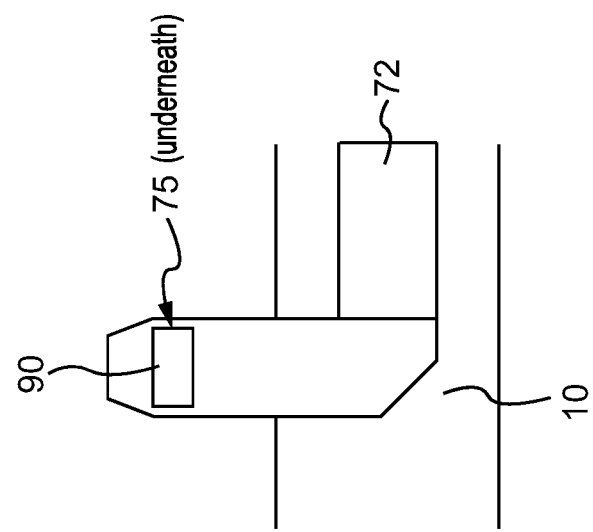
FIG. 21

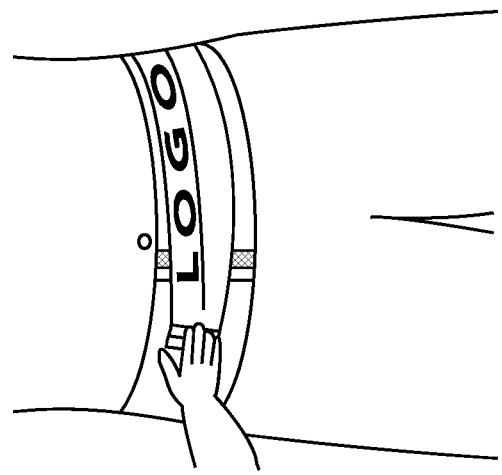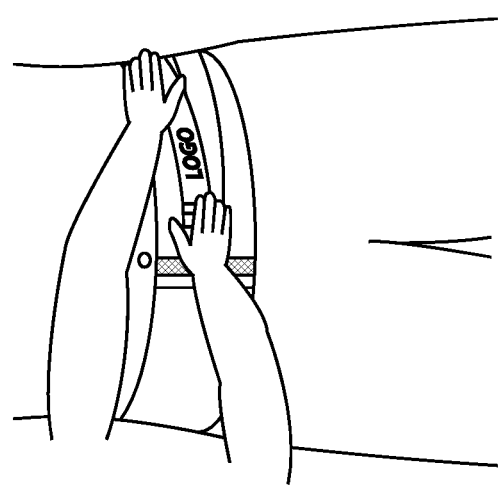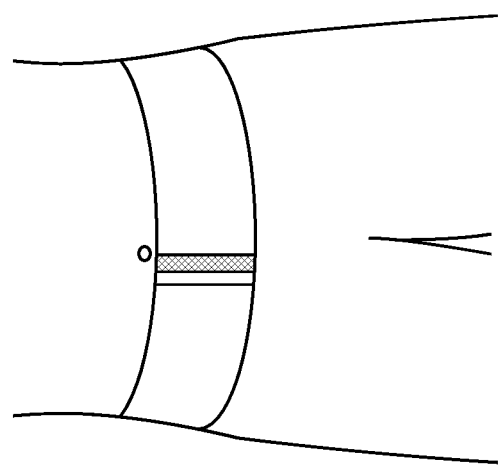
FIG. 22

ENDOSCOPY BAND WITH SIGMOID SUPPORT APPARATUS

CROSS-REFERENCE TO RELATED APPLICATIONS

This application is a continuation of U.S. application Ser. No. 15/256,019, entitled "METHOD AND APPARATUS FOR ENHANCED VISUALIZATION DURING ENDOSCOPY," and filed on Sep. 2, 2016, which is a continuation-in-part of U.S. application Ser. No. 13/344,715, entitled "METHOD AND APPARATUS FOR TENSILE COLONOSCOPY COMPRESSION," and filed on Jan. 6, 2012, and U.S. application Ser. No. 14/575,860, entitled "ENDOSCOPY BAND WITH SIGMOID SUPPORT APPARATUS," and filed on Dec. 18, 2014, which claims the benefit of U.S. Provisional Application Ser. No. 61/917,469, entitled "COLONOSCOPY BAND WITH SIGMOID SPLINT" and filed on Dec. 18, 2013, and U.S. Provisional Application Ser. No. 61/944,658 entitled "ENDOSCOPY BAND WITH SIGMOID SUPPORT APPARATUS" and filed on Feb. 26, 2014, and claims the benefit of priority of U.S. Provisional Application No. 62/214,747, entitled "IMPROVED BOWEL STABILITY AND ENHANCED VISUALIZATION DURING ENDOSCOPY" and filed on Sep. 4, 2015, the entire contents of each of which is expressly incorporated by reference herein in its entirety.

BACKGROUND

A colonoscopy is an examination of the large intestine or colon through the use of a colonoscope. A colonoscope is a flexible, tube-like inspection device having a camera at its end. Colonoscopies are performed for a variety of medical reasons including detection of inflamed tissue, ulcers, abnormal growths or polyps, and colorectal cancer. Colonoscopy as a screening tool to detect colorectal cancer has increased significantly since 2000.

During a colonoscopy, a colonoscope is inserted into a patient's rectum and then advanced to the beginning of the colon (an area known as the cecum) in order to examine the lining of the large intestine. The efficiency and accuracy of this procedure is largely dependent on the ease with which the colonoscope can be advanced. During the procedure, the colon may become over-distended or flopped in unnatural directions creating loops that hinder the advancement of the colonoscope and resulting in patient discomfort, longer examination times, and potentially inaccurate or incomplete screenings.

Currently, the difficulty in advancing the scope has been addressed by utilizing a surgical technician to manually support the patient's colon with pressure. This is time-consuming and dependent on the particular surgical assistant's strength, technique, and endurance, as well as training. Another way to apply differential pressure, particularly in larger patients, is to roll the patient from the left side to a supine or to a prone position. Often this is not an easy task with a sedated patient.

SUMMARY

In an aspect of the disclosure, a method and apparatus for applying pressure to the abdomen of a patient is provided to ease the passage of an endoscope during procedures used to examine the bowels including colonoscopy, sigmoidoscopy, and enteroscopy. Aspects presented herein exert both broad, uniform lower abdominal pressure as well as additional, location-specific pressure upon the sigmoid colon for the purposes of preventing and reducing the complication known as looping, eliminating the need for the application of manual pressure, improving patient safety, comfort, and satisfaction, and preventing musculoskeletal injury to endoscopy healthcare providers.

Additional advantages and novel features of aspects of the present invention will be set forth in part in the description that follows, and in part will become more apparent to those skilled in the art upon examination of the following or upon learning by practice thereof.

BRIEF DESCRIPTION OF THE DRAWINGS

FIG. 21 is a schematic view of a disposable, removable cover for the hook strip on the secondary strap, in accordance with aspects of the present invention. The depiction on the left shows the cover applied to the hook strip, and the depiction on the right shows the cover removed in preparation for use.

FIG. 22 is a perspective view of an endoscopy band device with a sigmoid support apparatus, comprising a detachable secondary strap with fastening mechanisms on each end that allow the secondary strap to be stretched along and secured to the exterior of the primary wrap in order to generate additional, location-specific compression, in accordance with aspects of the present invention. The three illustrations in FIG. 22 demonstrate the method of use of the apparatus.

DETAILED DESCRIPTION

The detailed description set forth below in connection with the appended drawings is intended as a description of various configurations and is not intended to represent the only configurations in which the concepts described herein may be practiced.

The detailed description includes specific details for the purpose of providing a thorough understanding of various concepts. However, it will be apparent to those skilled in the art that these concepts may be practiced without these specific details. In some instances, well known structures and components are shown in block diagram form in order to avoid obscuring such concepts.

Aspects presented herein comprise a primary abdominal wrap that is secured around the lower abdomen of the patient. Additional aspects may include any of a secondary strap and a shaped insert that provide directed force and support to the sigmoid colon. When the device is securely fastened, the secondary strap, the insert, or both, may be pushed, pulled, or otherwise pressed into the body in a manner that serves to support or 'splint' the sigmoid colon.

Figure 1C:
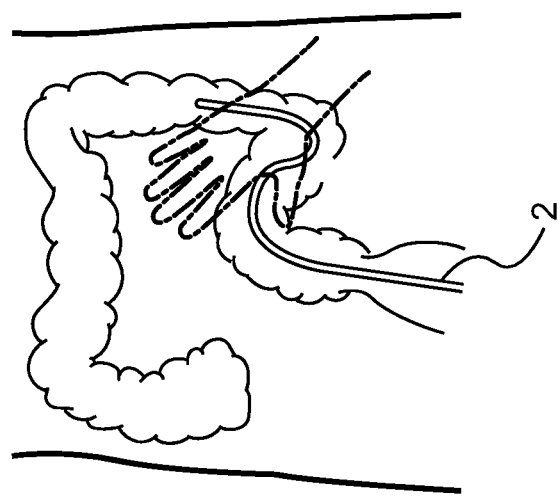
FIG. 1C is a schematic view of a colon showing the application of manual pressure to the colon to facilitate insertion of an endoscope.
Figure 1B:
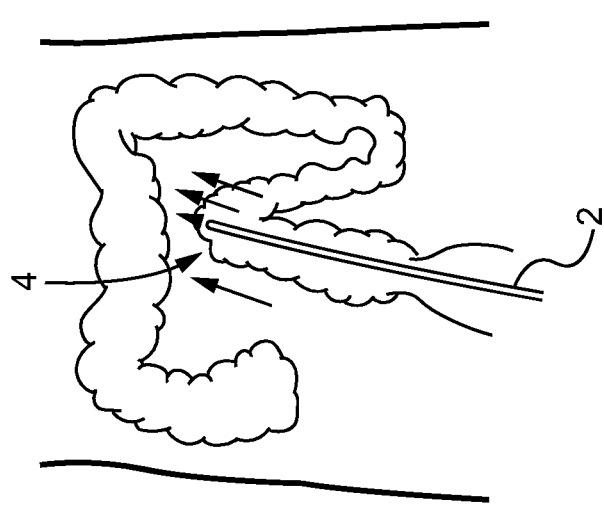
FIG. 1B is a schematic view of a colon in which a sigmoid loop has developed due to an attempt to advance the endoscope against an unsupported colon wall.
Figure 1A:
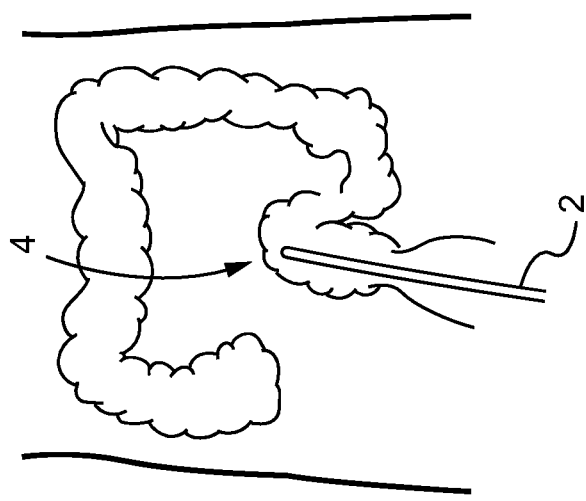
FIG. 1A is a schematic view of a colon with an endoscope (also known as a colonoscope for colonoscopy procedures) partially inserted therein.

Referring first to FIGS. 1A-C, there is shown in schematic form the sequence of steps of colonoscopy. In FIG. 1A, a colonoscope 2 is inserted into the patient's rectum and advanced forward through the length of the colon. As the operator passes the colonoscope through the sigmoid region of the colon 4, it often becomes impinged and causes distention and looping of the anatomy as shown in FIG. 1B. This causes discomfort to the patient and increases the time required for the colonoscopy. Additionally, in order to reduce the distended or looped area, the application of manual pressure to abdomen of the patient is often required. This pressure is generally applied by a nurse or surgical assistant as shown in FIG. 1C.

Figure 2B:
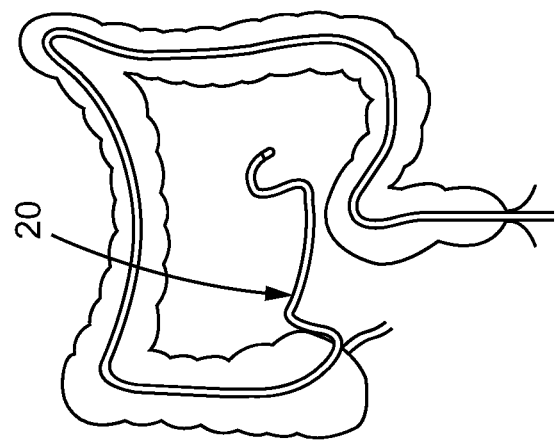
FIG. 2B is a schematic view of the performance of a retrograde enteroscopy.
Figure 2A:
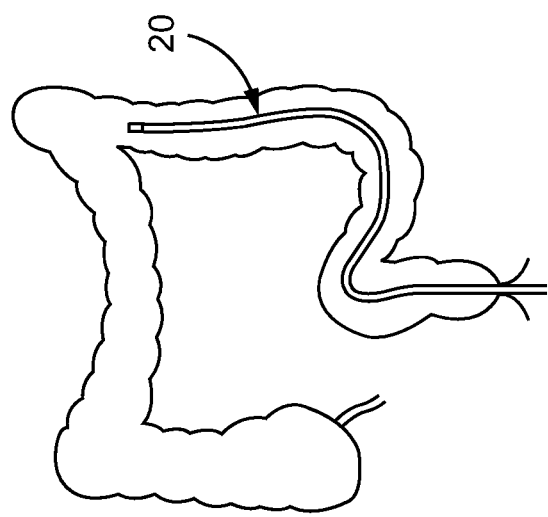
FIG. 2A is a schematic view of the performance of a sigmoidoscopy.
Figure 3A:
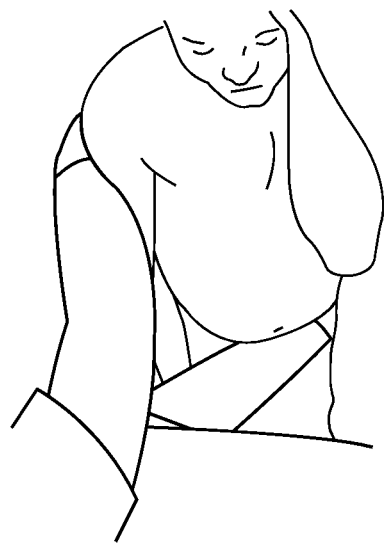
FIG. 3A is a perspective view of one method to apply manual pressure during a colonoscopy.
Figure 3B:
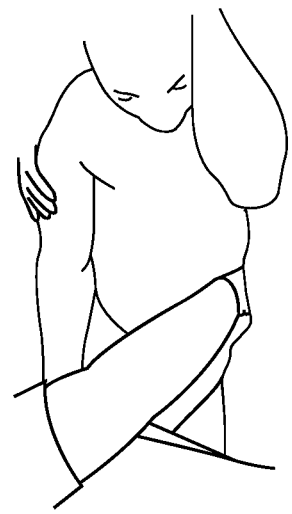
FIG. 3B is a perspective view of a second method used to apply manual pressure.
Figure 3C:
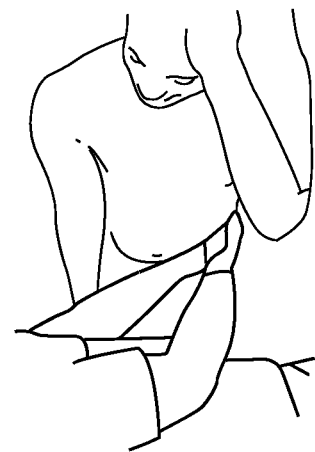
FIG. 3C is a perspective view of a third method used to apply manual pressure.

Referring to FIGS. 2A-B, there are shown in schematic form depictions of sigmoidoscopy and retrograde enteroscopy procedures, respectively. These figures are included to demonstrate the similarity between colonoscopy and these two additional endoscopic procedures. Sigmoidoscopy is an examination of only the lower part of the colon, from the anus to the descending colon. Thus, in FIG. 2A, an endoscope 20 is shown only inserted into the lower part of the colon Enteroscopy is an examination of the small bowel. During retrograde enteroscopy, an endoscope 20 is inserted in the anus and passed through the colon and the cecum and into the small bowel. Successfully navigating the loop-prone sigmoid region is necessary to complete both sigmoidoscopy and retrograde enteroscopy and thus application of the invention should help facilitate colonoscopy as well as sigmoidoscopy and retrograde enteroscopy.

Many patients undergo colonoscopy while placed in the left lateral decubitus position on the stretcher or operating table. FIGS. 3A-C 6-8 illustrate common methods used to deploy manual abdominal pressure when the patient is in this position. Additional information about the use of such manual pressure can be found in Prechel J A, Hucke R. Safe and effective abdominal pressure during colonoscopy: forearm versus open hand technique. Gastroenterol Nurs 2009; 32:27-30; quiz 31-2, the entire contents of which are incorporated herein by reference. Another frequently used method is for the nurse or assistant to reach over the patient from the opposite side of the table and to deploy pressure by placing their hands against the patient's sigmoid colon and then leaning backwards, using their bodyweight for leverage to exert force. While these methods are generally effective at generating pressure, they have also been identified as a causative factor for the high rate of work-related injuries among endoscopy nurses and staff. Physicians performing colonoscopy suffer work-related musculoskeletal injury at a particularly high-rate as well. The most frequent site of physician injury is the right upper extremity which experiences peak torque forces when while operators are attempting to advance the scope through (a looping) sigmoid colon. Additional details can be found in Spanarkel M, Hathorn J P. Looping During Colonoscopy: A Major, Implied Cause of Injury Among Endoscopy Healthcare Providers and a Proposed Solution, 2013, the entire contents of which are incorporated herein by reference.

Figure 4:
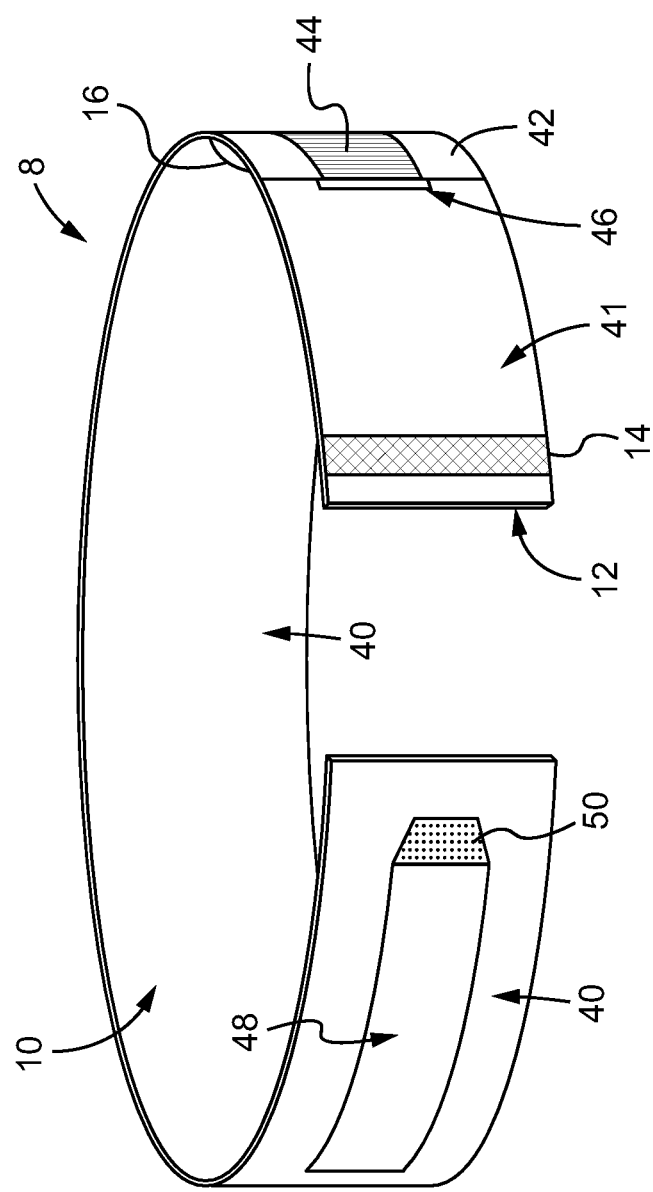
FIG. 4 is a perspective view of an unfastened endoscopy band device with sigmoid support apparatus, in accordance with aspects of the present invention.
Figure 5:
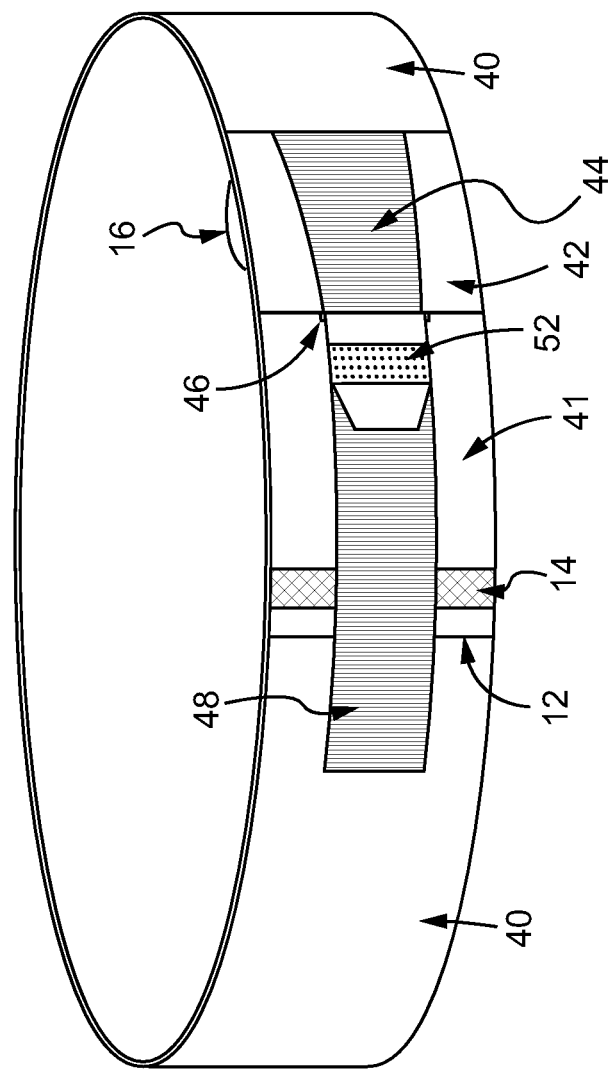
FIG. 5 is a perspective view of a fastened endoscopy band device with sigmoid support apparatus, in accordance with aspects of the present invention.
Figure 6:
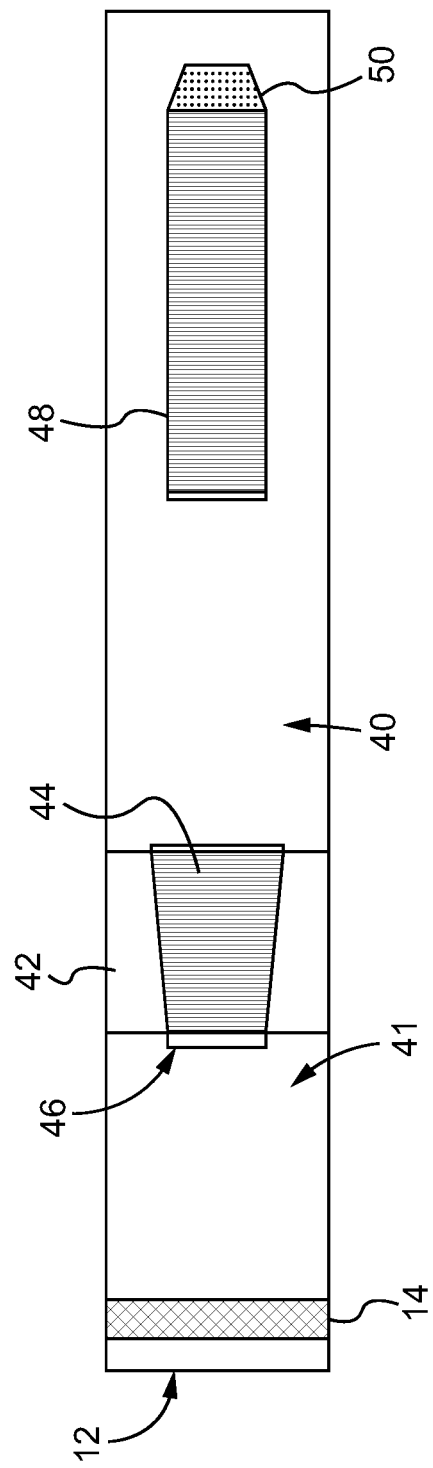
FIG. 6 is an overhead perspective view of the exterior side of the endoscopy band device with sigmoid support apparatus, in accordance with aspects of the present invention.
Figure 7:
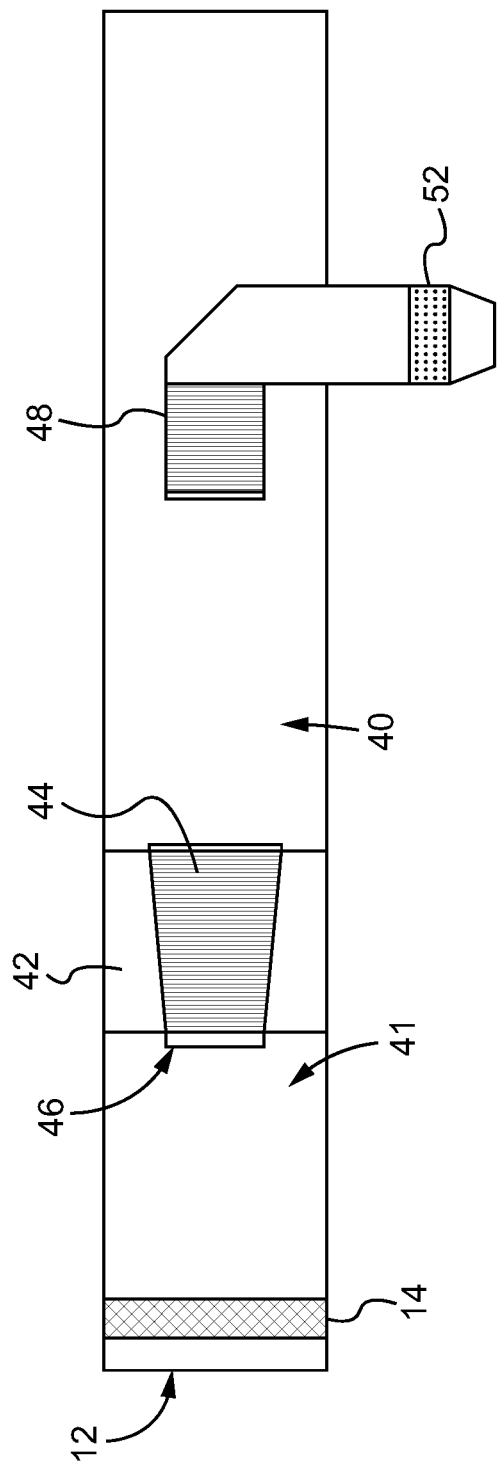
FIG. 7 depicts the same device FIG. 4, with the exception that in FIG. 5, the long secondary appendage attached to the primary band is folded over to show its handle.

As depicted in FIG. 4, the device 8 may comprise a primary elongated band or wrap 10 of sufficient length for placement around a patient's lower abdomen. A closing mechanism 12 may be provided at the end of the primary band to secure the device around the patient so that it provides the desired amount of broad support and compression. A handle 14 may be sewn onto the exterior of one or both ends of the primary wrap to assist in fastening and closure. Aspects may include, an insert 16 attached to the primary wrap 10 or used in conjunction with the primary wrap 10 to provide directed force to the sigmoid colon.

The primary wrap 10 preferably has a circumferential length between approximately 15 and 75 inches in order to accommodate varying abdominal girths in patients. The preferred width of the primary wrap 10 is between 6 and 10 inches, although variations having widths of between 3 and 20 inches may be used depending on the size of the patient and to accommodate special circumstances such as an abdominal hernia or a large pannus. For example, the primary wrap may be configured to have a width that allows it to be fastened around the patient's lower abdomen with the upper edge of the wrap just below the umbilicus and the bottom edge of the wrap along or close to the pubic line. The width of the primary wrap may be selected so as not to be so large that the upper edge conceals the umbilicus and additional areas of the abdomen above the umbilicus. This configuration may be made in order to avoid pressure on the diaphragm or stomach, as pressure on the diaphragm or stomach during colonoscopy can increase the risk of oxygen deprivation and aspiration events, respectively, due to the fact that the patient is generally sedated during the procedure. The primary wrap 10 may comprise, entirely or in part, a flexible, bio-compatible foam, rubber, neoprene, polyester, nylon, non-woven or woven fabric, mesh fabric, synthetic fabric, microfiber fabric, silicon or vinyl plastic, or any other materials generally known to be used in medical fabrics and goods. The primary wrap 10 may be composed of both elastic and inelastic materials.

For the primary wrap to provide appropriate general compression and support, it may be important that the wrap remain flat against the body when fastened around the abdomen. This is notable because certain materials and designs have a tendency to roll-up when stretched or wrapped around the abdomen, particularly when the device is being applied to patients with a large pannus. To prevent roll-up from occurring, aspects of the invention may include reinforcements to ensure that the primary abdominal wrap remains flat against the body when used in patients of varying body sizes. This may be accomplished by the application of serge stitching along the edges of the primary abdominal band.

Next, the primary wrap may also accommodate an insert or attachment that provides specific support to the sigmoid colon. The insert may be held against the patient's body by a nurse or assistant, and then the primary wrap be fastened around the patient's abdomen and overtop of the insert. This causes the insert to be positioned between the patient's abdomen and the wrap. The wrap helps to maintain the insert at the desired placement and applies pressure to the insert. Alternately, the insert may be attached to the primary wrap by an adhesive, Velcro, or magnets while the primary wrap is fastened. In as aspect, there may be a pouch sewn or otherwise attached to the primary wrap into which the insert may be placed. The insert may also be embedded in the wrap. Such a pouch may be accessible on the interior, exterior, or both sides of the primary wrap, providing the user the option to add the insert to the primary wrap when deemed necessary. In an alternative embodiment, the insert may be sewn or attached into or onto the primary wrap during manufacturing and in this case may be a non-removable, inherent product feature. In other aspects, the actual insert may be incorporated into the primary wrap during manufacturing, and certain appendages may emerge or extend from the insert or the pouch in which the insert is placed. These appendages may be used, e.g., to facilitate the measurement of the force generated by the insert upon the patient's abdomen, the monitoring of vital signs, or the capture of other data relevant to the patient's health and safety.

The insert may comprise materials that, when pushed, pulled, or otherwise pressed against the patient's abdomen, are able to provide moderate to firm direct force to the sigmoid colon, without causing discomfort or pain for the patient or impeding the colonoscopy procedure in any way. In one example, the insert may comprise a firm foam material. In another example, the insert may comprise a semi-flexible plastic, in a third, a semi-flexible silicone composite, and in a fourth, an inflatable plastic or composite air bladder. The insert may additionally comprise paper, rubber, neoprene, or fabric, or a combination of any of these materials or those listed in the previous sentence, and also in conjunction with a hard object around which these materials are wrapped. An important aspect of the composition of the insert may be that, when it is compressed into the abdomen, it be firm enough to exert counter-pressure that is sufficient to 'splint' the sigmoid colon and facilitate the passage of the scope, but flexible enough that in providing counter-pressure, it does not hinder the passage of the scope instead.

Figure 10:
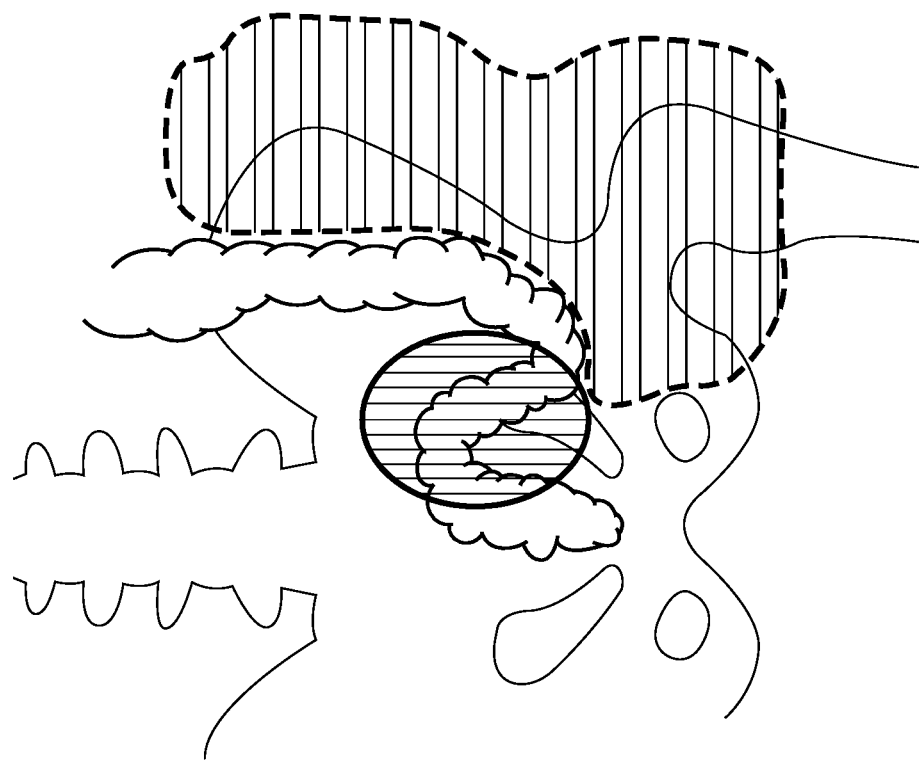
FIG. 10 is a schematic view of the target area for sigmoid compression as well as the anatomical features, particularly the left hip, pelvis, and pubic bones, that could impede the ability of an insert to compress the sigmoid colon if the insert is too large or improperly designed, in accordance with aspects of the present invention.

Another important element of the insert may be its size. While the insert used in the invention may vary to accommodate differing body types and sizes, any insert used may be of a size that, when positioned over the sigmoid colon, is capable of being compressed into the left lower quadrant of the abdomen generally, and the sigmoid colon specifically, without it being impeded by any other anatomical feature. Relevant anatomical features that may be accounted for include the left pelvis and hip. FIG. 10 depicts an example target area on the body for compression, with the hashed-area in the drawing indicating the anatomical features that might impede the insert in compressing the sigmoid colon if the size of the insert is too large.

Figure 8:
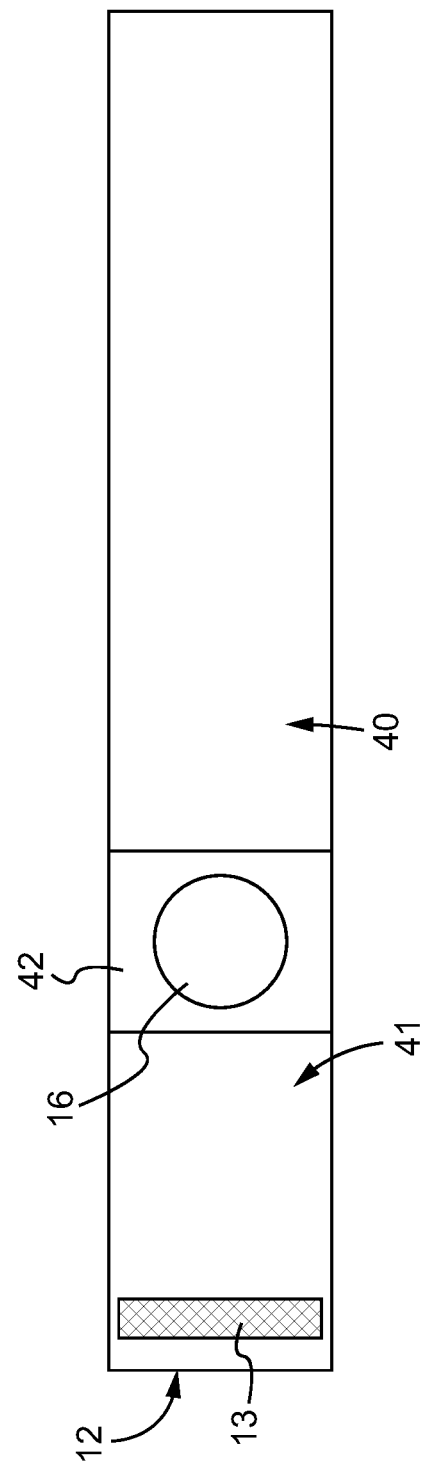
FIG. 8 is an overhead perspective view of the interior side of the endoscopy band device with sigmoid support apparatus, in accordance with aspects of the present invention.
Figure 9:
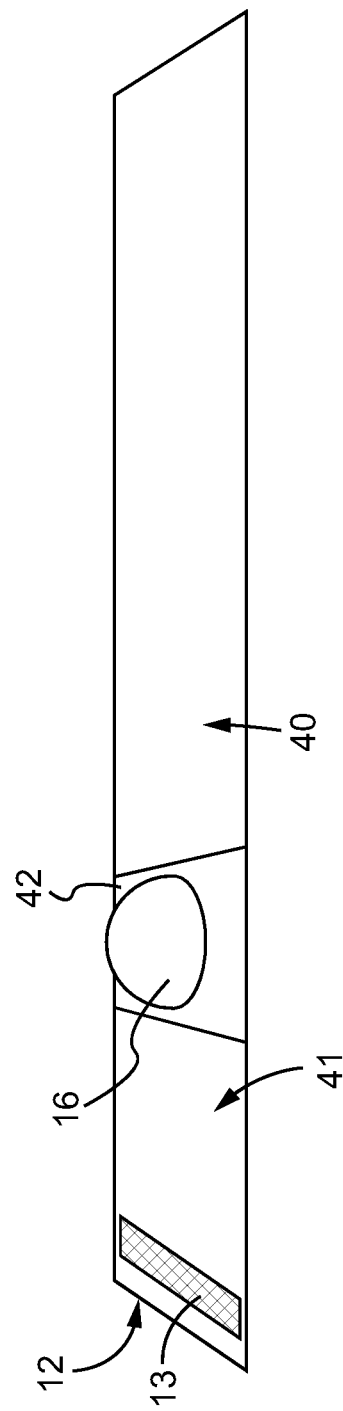
FIG. 9 is an angled overhead perspective view of the interior side of the endoscopy band device with sigmoid support apparatus, in accordance with aspects of the present invention.
Figure 11:
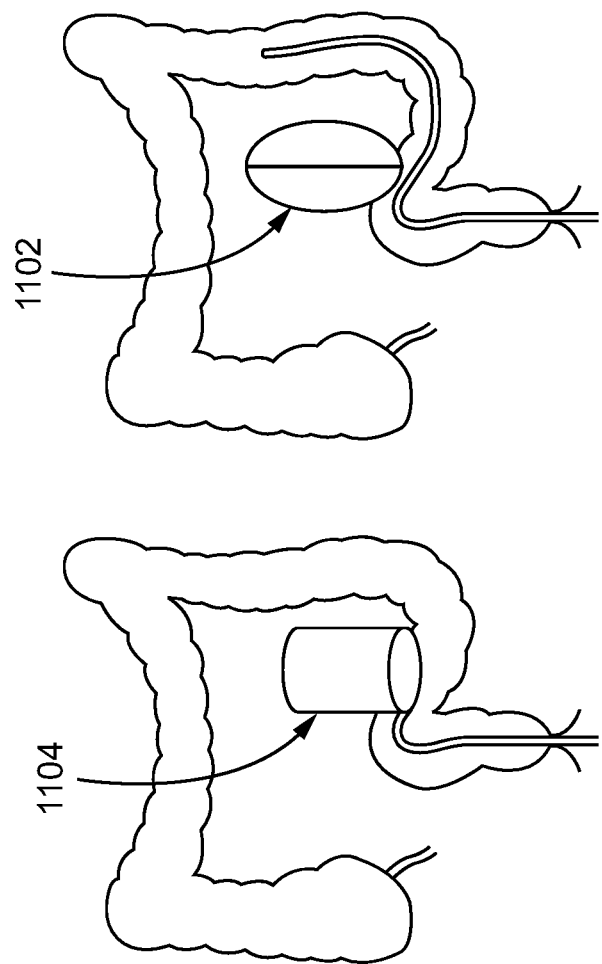
FIG. 11 is a schematic view of the colon, and specifically of the application of pressure to the sigmoid colon by a non-tapered insert (drawing on left) versus tapered insert (drawing on right), in accordance with aspects of the present invention. The non-tapered insert is hindering the advancement of the colonoscope.

Another important aspect of the insert may be the shape of the insert. The insert shape may be configured to provide firm pressure to the sigmoid colon without pinching the colon or compressing the lumen in a way that impedes the advancement of the colonoscope. Aspects presented herein address this concern by tapering the edges of the insert to reduce the likelihood of the insert pinching or closing of the colon when compressed by the device. In one embodiment, the shape of the insert may approximately resemble the shape of a small souvenir football. When deployed, this insert may be placed in either a horizontal or vertical orientation. FIG. 11 illustrates an example tapered insert 1102, placed in a vertical orientation, alongside an example of a non-tapered insert 1104 in order to illustrate the potential for the non-tapered insert to pinch the colon and hinder the advancement of the scope. In another example, the shape of the insert may resemble a semi-hemisphere, with the flat side of the insert placed against the wrap and the circular side of the insert held against and pressed into the patient's sigmoid colon. An example of a semi-hemisphere insert 16 is illustrated in FIGS. 8 and 9.

Additionally, the insert may offer additional functionality beyond applying force to the sigmoid colon. Through testing, a standard may be developed that identifies and recommends the optimal amount or range of force needed to optimally support the colon in various patient groups. Accordingly, having some type of force measurement system built into the insert may be a natural way to provide device operators with knowledge regarding the amount of force they are exerting on the patient's sigmoid colon. Having such knowledge could improve the safety, consistency, and effectiveness of the device and the application of pressure during a colonoscopy generally.

There are several ways in which the insert may be configured to measure force. In one aspect, springs may be built into the insert that, when compressed, render a force output on a small, mechanical display. This may function in a manner similar to a non-digital bathroom scale. The display may be positioned in a location where it can be easily read by the physician, nurse, or assistant.

In another aspect, the pouch, or exterior portion of the wrap where the pouch is located, or both, may be made of a transparent material that allows for the scale to be read. For example, the scale may be built into the insert on the side opposite the patient.

In another aspect, load cells that provide a force output to a digital scale may be built into the insert, and may be powered by either insertable, rechargeable, or finite-use batteries incorporated into the insert during manufacturing.

Another aspect may be designed to reduce complexity, by establishing optimal pressure standards through testing. Once optimal pressure standards are identified, the insert may be designed to render a simple binary or ternary output indicating the relationship of the pressure currently applied to that of the identified optimal pressure, e.g., that the pressure applied is not enough, too much, or correct.

In another aspect, an air bladder may be incorporated into the insert for facilitating force measurement. In this example, the air bladder inside the insert may include a protruding tube that extends outside of the insert. The tube may be capable of being connected to a tool for measuring pressure such as a sphygmomanometer. For example, the user may measure the baseline pressure of the air bladder prior to the insert being compressed, and then may be able to calculate the force applied to the patient by comparing the difference between the observed pressure and the baseline value.

Aspects described herein may be designed to provide broad lower abdominal support, and additional direct force to the sigmoid colon of a patient undergoing colonoscopy.

Additional aspects include a device configured to provide directed force to the sigmoid colon. This may involve, e.g., the incorporation of various different features. A first example may include a primary abdominal band comprising two or more sections that vary in material type. In one example, as depicted in FIG. 9, two sections—one larger 40, and one smaller 41—of the primary abdominal band 10 may be composed of a flexible, elastic or semi-elastic, medium-thickness, latex-free neoprene with thin polyester or nylon glued to its interior and exterior sides. Among others, this material may be capable of providing broad, firm, yet comfortable support to the patient's abdominal region. A third section 42 of the primary wrap 10 may comprise a relatively inelastic material, such as a woven fabric. The inelastic section 42 may be provided at the location into which or under which the insert is placed. Upon deployment of the device, the inelastic section 42 may be positioned in the patient's lower left abdominal quadrant, over the sigmoid region. The primary wrap 10 may be placed around the patient's lower abdomen and secured using a closing mechanism 12 consisting of a strip of VELCRO® or hook material 13 placed on the interior of the wrap 10 close to the location of the handle 14 on the opposite side. This hook strip 13 may be fastened to the exterior side of the opposite end of the primary wrap 10.

The edges of the hook strip 13 might not extend to the edges of the primary wrap 10. This construction may be designed to minimize the chance that the hook strip 13 comes into contact with the patient's skin, or with the gloves of the nurse or assistant deploying the device, as there is a small but known risk of VELCRO®, or a hook and pile material, being capable of tearing medical gloves.

An additional feature designed to reduce the likelihood of patient and provider contact with the hook material is depicted in FIG. 21. In aspects incorporating this feature, prior to the device being packaged, a thin layer of material 90 may be applied to hook strips that are incorporated into the device. This layer 90 may comprise, e.g., paper, plastic, fabric, silicon, or any other biocompatible material typically used in healthcare products. Additionally, the layer 90 may be lightly adhered to the hook strips so that it remains in place—until it is easily removed and disposed of by the end user just prior to the device's application on the patient. This feature may be especially helpful in examples that include a secondary strap, such as the device depicted in FIG. 16. This is because in such devices, it may be important that the secondary strap 72 remain unfastened until the primary wrap 10 is fastened and properly positioned. Having a layer 90 covering the hook strip 75 on the secondary strap 72 helps to ensure that the secondary strap will not be accidentally fastened while the user is securing the primary wrap 10 around the patient's abdomen.

In one example, there are one or more appendages on the exterior of the primary wrap that facilitate the application of additional directed force by the insert, e.g., without requiring adjustment of the primary wrap. The appendages may comprise one, or several, straps attached on one side to the edge or edges of non-elastic section. On the unattached end of these straps, there may be a closing mechanism. The straps may be pulled horizontally along the exterior of the primary wrap, and fastened using the closing mechanism securely enough to maintain tension. When these straps are secured to the inelastic section, the tension generated by fastening these straps causes additional compression of the inelastic section and the insert being toward the body.

Figure 12:
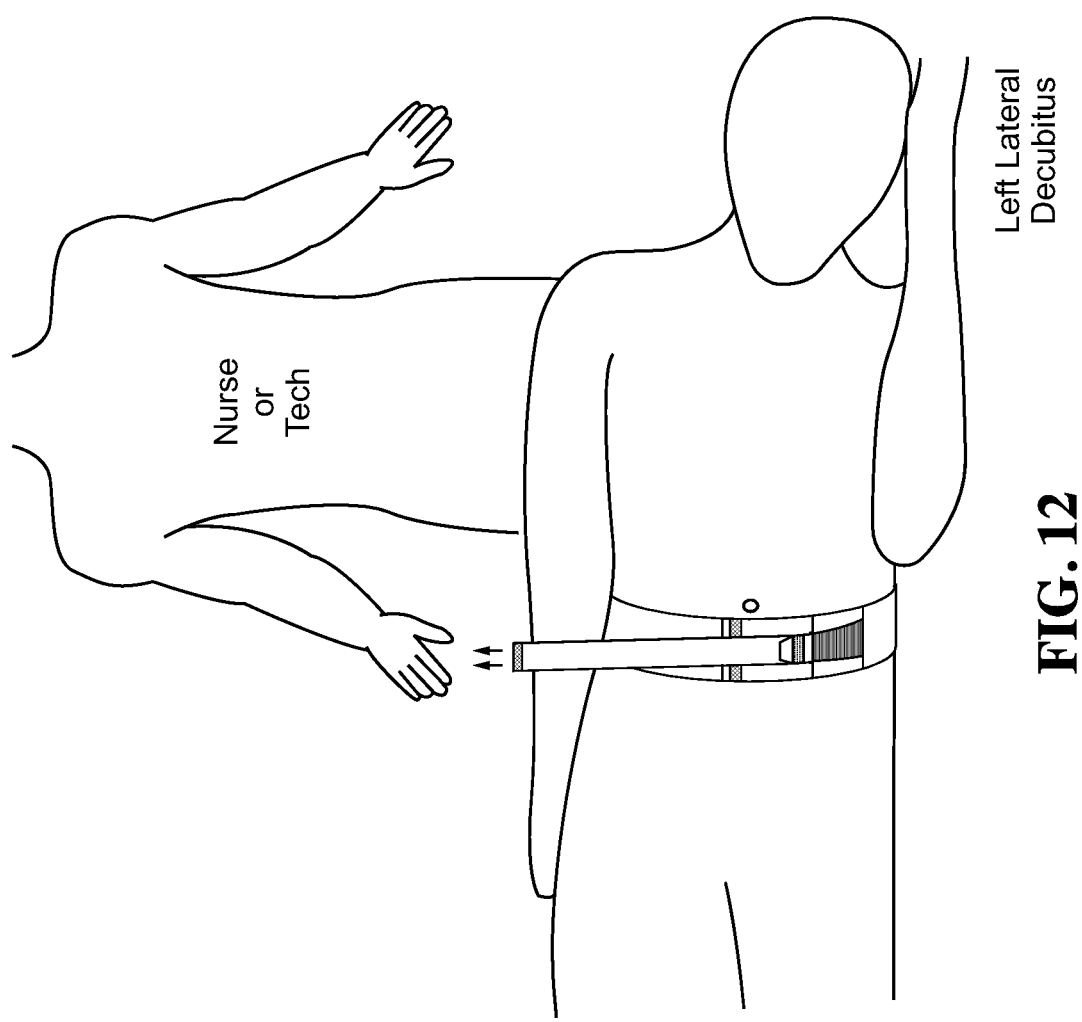
FIG. 12 is an illustration to show how the level of sigmoid compression exerted by the device during the procedure may be adjusted, in accordance with aspects of the present invention.
Figure 13:
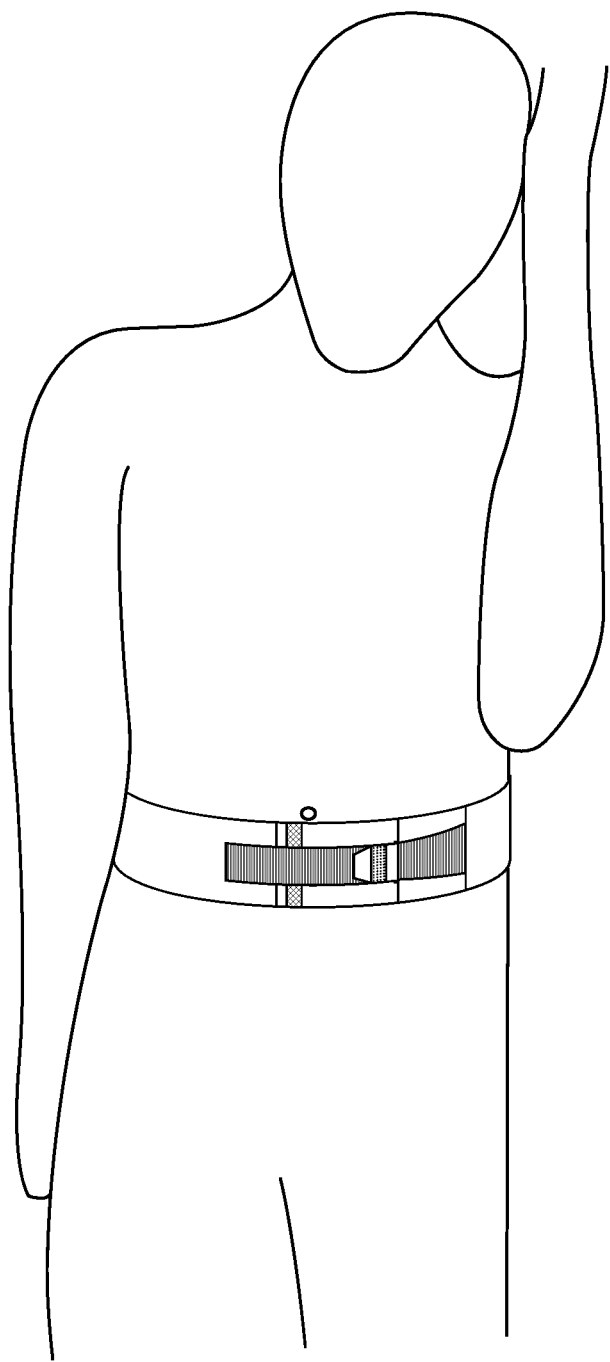
FIG. 13 is an illustration of a patient lying in the left lateral decubitus position with the device secured around his lower abdomen, in accordance with aspects of the present invention.

As depicted in FIGS. 4-7, a short strap 44 may be attached along its own right vertical edge to the right vertical edge of the inelastic section 42. The strap 44 may lay to the left, and extends just past the left vertical edge of the inelastic section 42. On the end of the strap 44 not attached to the inelastic section 42, there may be a small hinge 46. There may also be another, longer strap 48 attached along the larger neoprene section 40 of the exterior primary wrap 10. The longer strap 48 may be positioned approximately midway along section 40. Once the primary wrap has been fastened by its closing mechanism 12, this strap 48 may be passed across the closing mechanism 12 of the primary wrap 10, through the hinge 46 on the short strap 44, and then doubled-back and pulled toward the direction from which it came. At the unattached end of the long strap 48, there may be a patch of VELCRO® or hook material 50 (visible in FIG. 4, 6), and on the opposite of the side of this end of the long strap 48, a small handle 52 (visible in FIGS. 5, 7.) Once the strap 48 passes through the hinge 46, this strap may be tightened and fastened by the nurse or assistant to exert additional, directed force to the sigmoid colon through the insert 16. As depicted in FIG. 12, this aspect may allow nurses and technicians to easily adjust the force on the sigmoid colon from the location in the procedure or operating room in which they are most often positioned during a colonoscopy, It additionally eliminates the need for the nurse or assistant to provide manual abdominal compression, thereby reducing their risk of musculoskeletal injury. Additionally, this example allows for the device to be quickly and easily removed should the need arise.

Thus, as illustrated in FIG. 12, the strap is coupled, e.g., sewn, to a portion of the wrap that is configured for placement over a left side of the patient's lower abdomen. The strap is pulled from left to right, e.g., pulled across lower abdomen and left lower abdominal quadrant from left side of body towards right side of body. This can be helpful because the patient typically lies on their left side during the procedure. Because the strap pulls from left to right across the lower abdomen, additional leverage and compression may be generated by the patient's body when the strap is in place. As the strap goes from left to right also allows the level of compression generated by the device to be easily adjusted during the procedure, e.g., while the patient is lying on their left side.

Thus, the strap is connected to the wrap in a manner that it extends under the patient during a procedure. The strap can then be pulled opposite the portion under the patient in order to use the weight of the patient's body to adjust the compression applied by the strap.

The wrap may be re-usable and washable, re-usable with a finite number of uses, and/or disposable and designed for single-use only. In addition, aspects may comprise a combination of re-usable and disposable parts. In disposable aspects, features may be incorporated into the device that indicate whether the product has been previously used. These features may include materials that change color, shape, size, or composition after the product has been used once. Additional features may include coloring the exterior of the wrap white or another light color so that evidence of use and soiling is obvious.

Other aspects might not use the insert to indicate, gauge, or measure the amount of force being generated upon the sigmoid colon or the lower abdomen. Certain aspects may instead utilize mechanical and visual indicators to inform device operators how or where to fasten the invention to exert optimal pressure to facilitate the procedure. Several examples are depicted in FIGS. 14-15.

Figure 14:
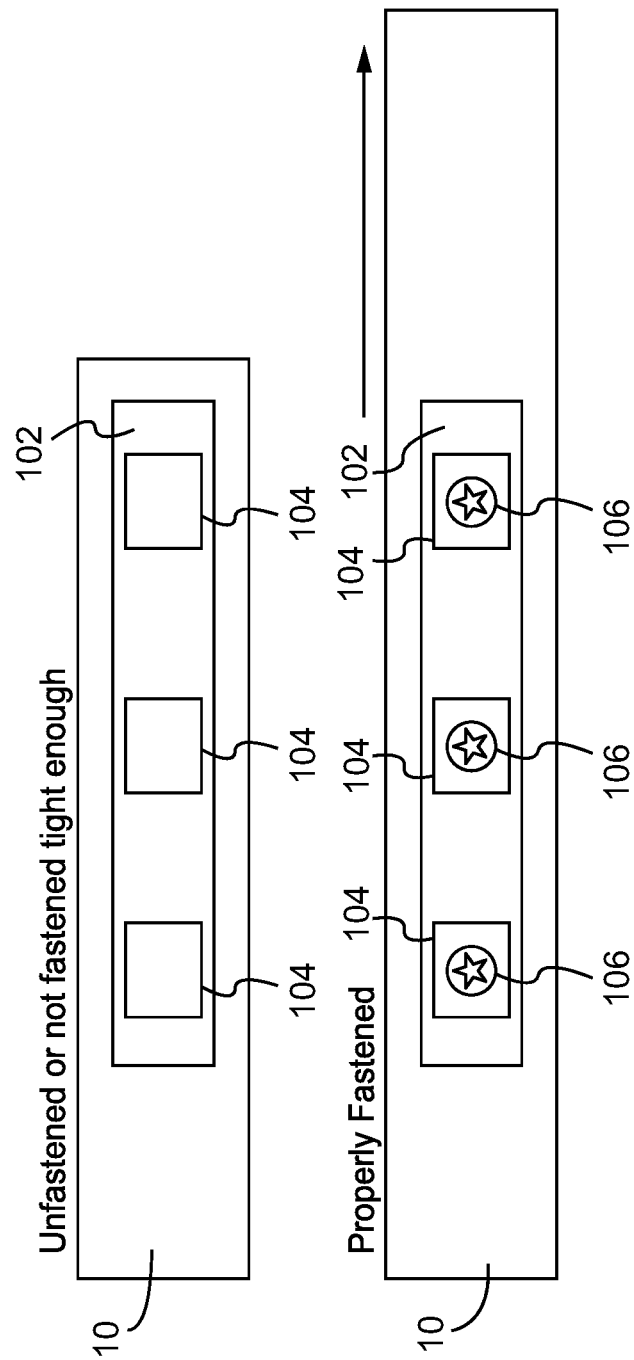
FIG. 14 is a schematic view of a mechanism for indicating that the primary wrap or secondary strap is sufficiently fastened, in accordance with aspects of the present invention, and includes a non-elastic strip with windows attached to the exterior of the band, and in which icons or images become visible once the device is sufficiently fastened.

One aspect, illustrated in FIG. 14 incorporates a non-stretchable strip 102 with transparent windows 104 attached to the exterior surface of the primary wrap 10, or alternatively to the exterior surface of a secondary strap. When the wrap is stretched or fastened sufficiently, visual indicators such as logos 106 may, for example, become visible through the transparent windows 104.

Figure 15:
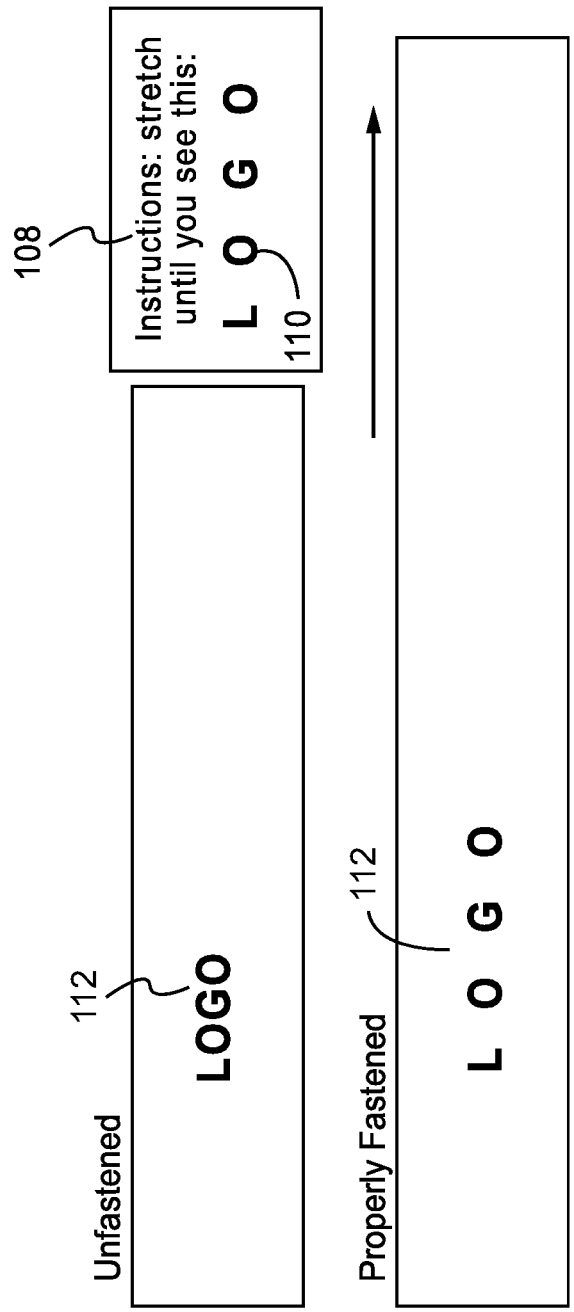
FIG. 15 is a schematic view of a mechanism for indicating that the primary wrap or secondary strap is sufficiently fastened, in accordance with aspects of the present invention, and includes an image or logo on the exterior side of the primary wrap needing to be stretched and distorted until the image on the wrap matches the image depicted in the user instructions. Matching of the images indicates that the device is properly fastened.

Another aspect, illustrated in FIG. 15 may include instructions to the user 108 to stretch the primary wrap 10, or a secondary strap (not shown) until a visual indicator such as a logo 112 on the exterior of the primary wrap 10 is distorted, e.g., stretched, to the point that it looks like the visual indicator included in the instructions 110. The matching of the images may be used to indicate to the user that the device has been properly fastened.

In another aspect, sensors capable of being stretched may be attached to the exterior surface of the wrap or secondary strap. These sensors may be built into a circuit with a small battery and LED light, all of which may be sewn into or attached to the wrap. When the sensors are stretched, the resistance in the circuit may be altered. The circuit may be designed to light the LED when the desired amount of stretch and resistance has been achieved.

Figure 16:
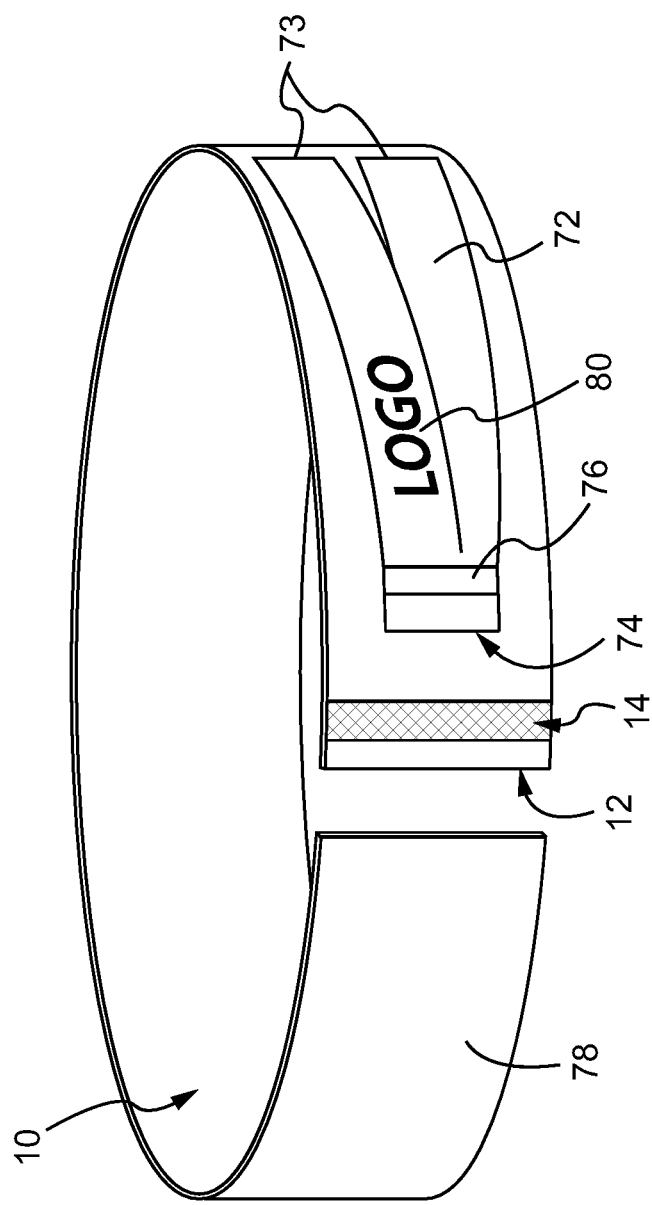
FIG. 16 is a perspective view of an unfastened endoscopy band device with a sigmoid support apparatus, in accordance with aspects of the present invention, the device comprising an elastic secondary strap capable of retaining tension and exerting directed force to the sigmoid colon when stretched and fastened to the primary wrap.
Figure 17:
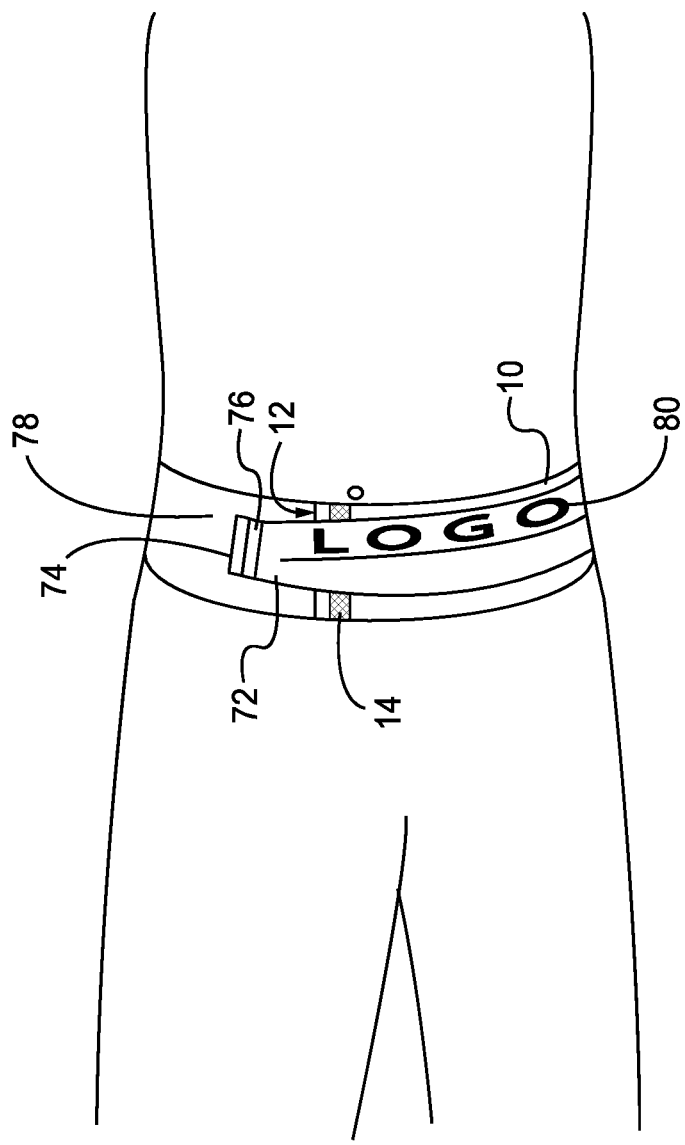
FIG. 17 is a perspective view of the endoscopy band device depicted in FIG. 16 as it appears when applied to a patient, in accordance with aspects of the present invention, shown while the patient lies in the left lateral decubitus position.

Additional example aspects of the device are depicted in FIGS. 16-17, and may include a primary wrap 10, with a closing mechanism 12, and a handle 14 to assist in fastening the primary wrap around the patient's lower abdomen. The device may also include a secondary strap 72 attached to the exterior side 78 of the primary wrap 10, with a closing mechanism 74 that allows the strap, e.g., to be fastened to the exterior side 78 of the primary wrap 10. In an aspect, the closing mechanism 74 of the secondary strap 72 may comprise a hook strip 75 on the inside of the secondary strap 72 that is capable of fastening anywhere along the exterior side 78 of the primary wrap 10—the hook strip 75 on the secondary strap 72 is visible in FIG. 21. In this example, the exterior side 78 of the primary wrap 10 comprises a hook-compatible material to which the hook strip 75 can be fastened and remain fastened while the secondary strap is stretched and under tension. The secondary strap 72 is constructed of an elastic or semi-elastic material that is capable of retaining tension when stretched horizontally and fastened to the exterior side 78 of the primary wrap 10 using the closing mechanism 74. The secondary strap 72 may comprise the same or different materials than the materials comprised in the primary wrap 10. The secondary strap 72 may comprise one or more layers of materials. In an example, the secondary strap 72 may comprise an elastic strap the entire length of which equals approximately twice the intended length of the secondary strap 72. In this example, the elastic strap may be doubled-over, and both ends may be sewn to the exterior 78 of the primary wrap 10 along the same vertical line 73, creating the horizontal 'V' appearance of the secondary strap 72 shown in FIG. 16. Doubling-over the material composing the secondary strap can serve to increase the breadth and force generated by the secondary strap, while preventing the incurrence of additional materials costs that would be associated with using a taller, single-layered strap instead. The midpoint of the secondary strap may be positioned approximately over the patient's lower left quadrant once it is stretched and fastened.

An insert may or may not be used with this example. Should an insert be used with this embodiment, the insert may be positioned against the exterior side 78 of the primary wrap 10, in the preferred anatomical location. Once properly positioned, the secondary strap 72 may then be passed over the top of the insert, stretched to tension, and fastened using the closing mechanism 74. The force exerted upon the insert by the tensioning of secondary strap 72 may serve to press the insert into the body in manner that allows the insert to successfully splint the sigmoid colon. Mechanisms for indicating stretch and compression, such as those described in connection with FIGS. 14 and 15, may be provided so that the device includes a mechanism to visually indicate the magnitude of force being applied, such as the mark 80 labeled "Logo" which stretches and deforms when the secondary strap 72 is stretched and fastened. With this mechanism, users may compare the deformed mark with a picture or illustration included in the product instructions or packaging to determine that the device has been applied correctly.

Figure 23:
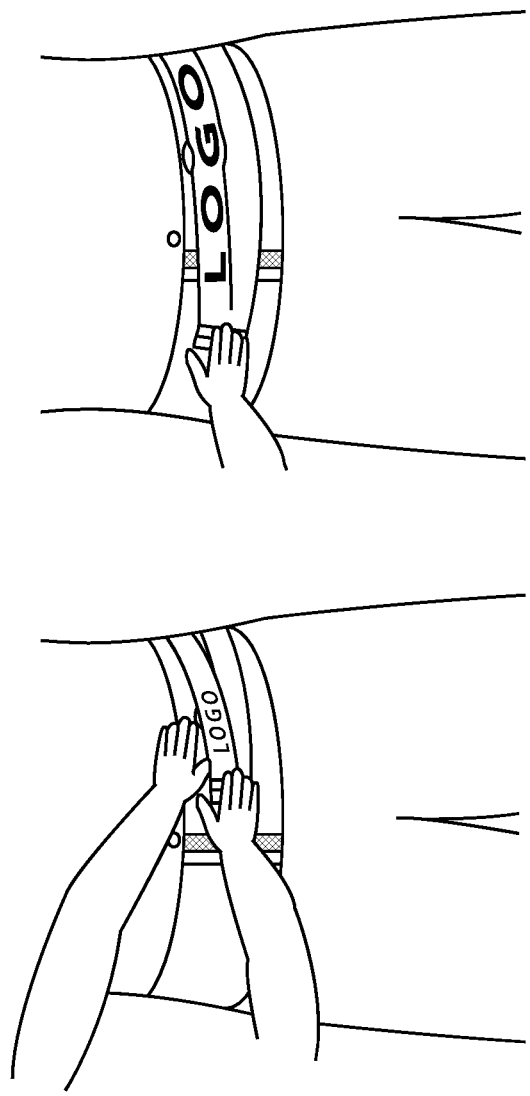
FIG. 23 is a perspective view of the operation of the endoscopy band device and detachable secondary strap depicted in FIG. 22 when the apparatus is used in conjunction with an insert as a means to provide focused compression and support, in accordance with aspects of the present invention.
Figure 24:
FIG. 24 is a perspective view of an endoscopy band device and insert, with the band comprising a strap capable of retaining tension when stretched, with fastening mechanisms on each end that allow the strap to be safely, comfortably, and firmly secured or adhered to the patient, with the strap passing over top of the insert, such that when the strap is secured, the insert is forced into the patient's body, in accordance with aspects of the present invention. The three illustrations in FIG. 24 demonstrate the method of use of the invention, applied while the patient is undergoing colonoscopy and lies in the left lateral decubitus position.
Figure 25:
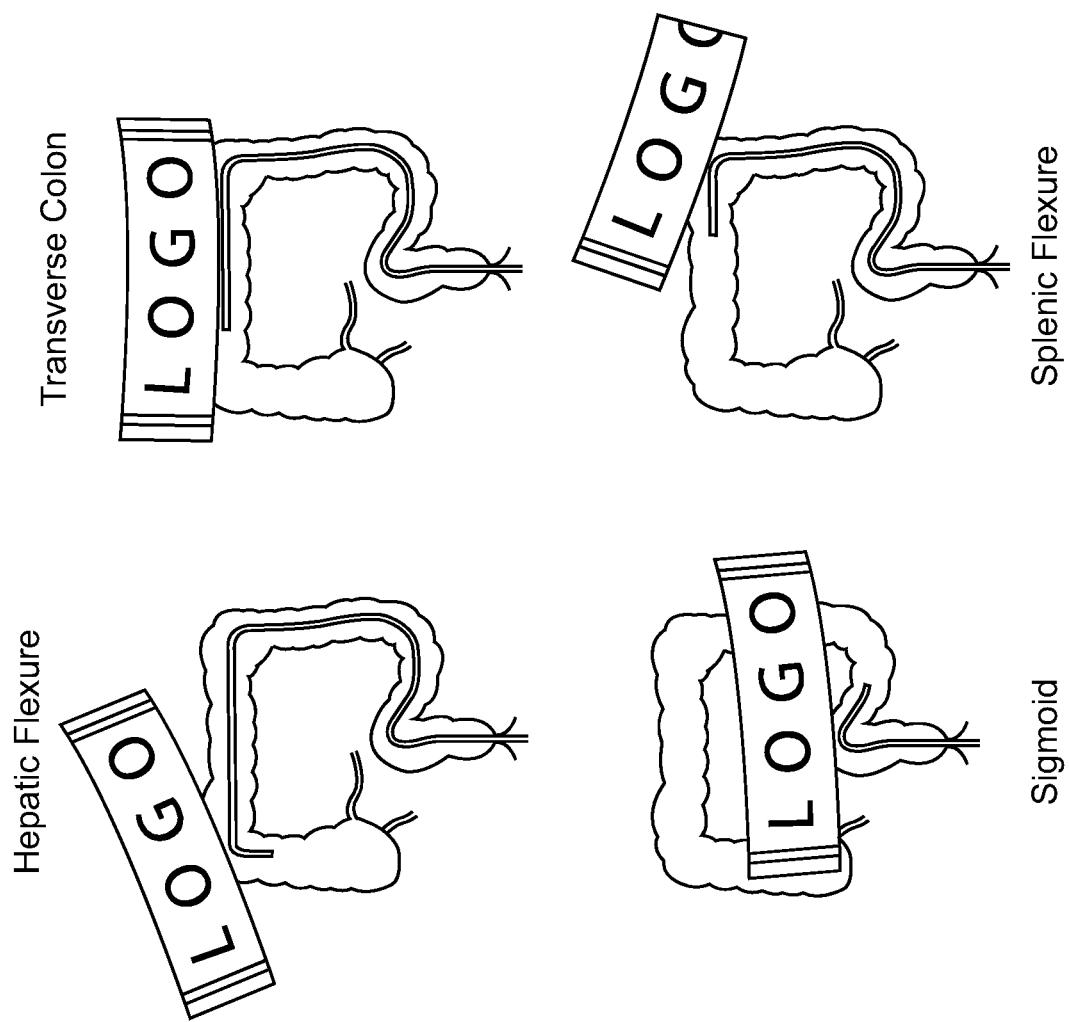
FIG. 25 is a schematic perspective of the sigmoid colon and three additional anatomical locations (splenic flexure, transverse colon, and hepatic flexure) where looping is known to occur and where the application of various aspects of the invention could facilitate and improve the procedure.

Other aspects may also incorporate a secondary strap to exert additional, location specific force is depicted in FIGS. 22-23. Unlike the embodiment depicted in FIG. 16, where one-side vertical side of the secondary strap is affixed to the device, the secondary strap in the embodiment shown by FIGS. 22-23 may be fully detachable from the primary wrap, and may have fastening mechanisms at both ends that allow the strap to be secured the exterior side of the primary wrap. The secondary strap in this aspect may be either re-usable or disposable, and may be capable of being stretched and maintaining tension, or may use another mechanism to exert compressive force, when it is secured to the primary band. An insert may be used with the detachable secondary strap, as demonstrated in FIG. 23. FIG. 24 depicts an example that includes only one strap. The strap in this example might not wrap fully around the patient but instead may be stretched directly about the location on the patient's body where force is desired. The strap may be equipped with fastening mechanisms on each end, e.g., to allow the strap to adhere directly to the patient's body. Such a wrap may be used with an insert. The insert may be separate from the strap, or may be affixed to or build into the strap. The strap and insert in this embodiment may be either re-usable or disposable. Such aspects might be particularly helpful in instances when unexpected looping occurs, particularly in areas of the bowel less prone to looping. FIG. 25 illustrates schematically how the wrap may be used to address looping at the splenic flexure, in the transverse colon, or at the hepatic flexure.

Improving patient comfort and reducing complications, both during and following endoscopic procedures is very important. Aspects presented herein reduce patient discomfort and complications by helping to prevent and reduce sigmoid looping, which can be a primary cause of patient pain and discomfort.

Figure 18:
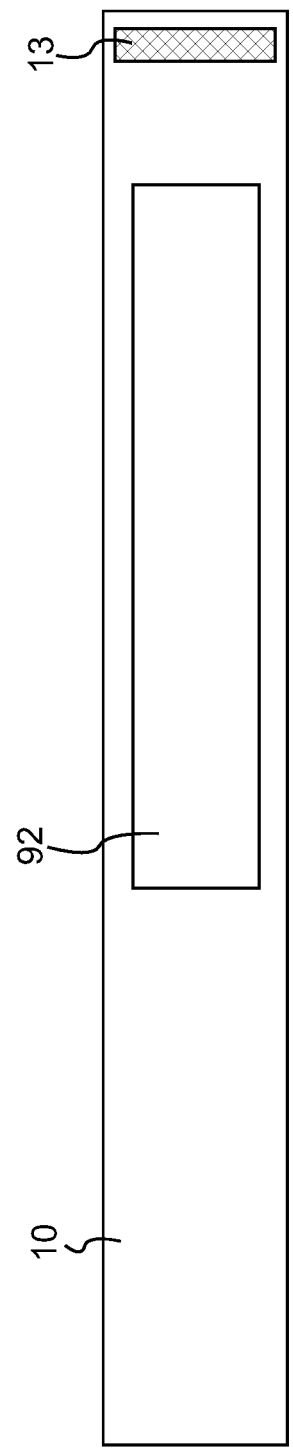
FIG. 18 is a schematic view of an endoscopy band device that includes a pouch on its interior side that can be used to hold heating pads and materials that provide the patient warmth and comfort, in accordance with aspects of the present invention.
Figure 19:
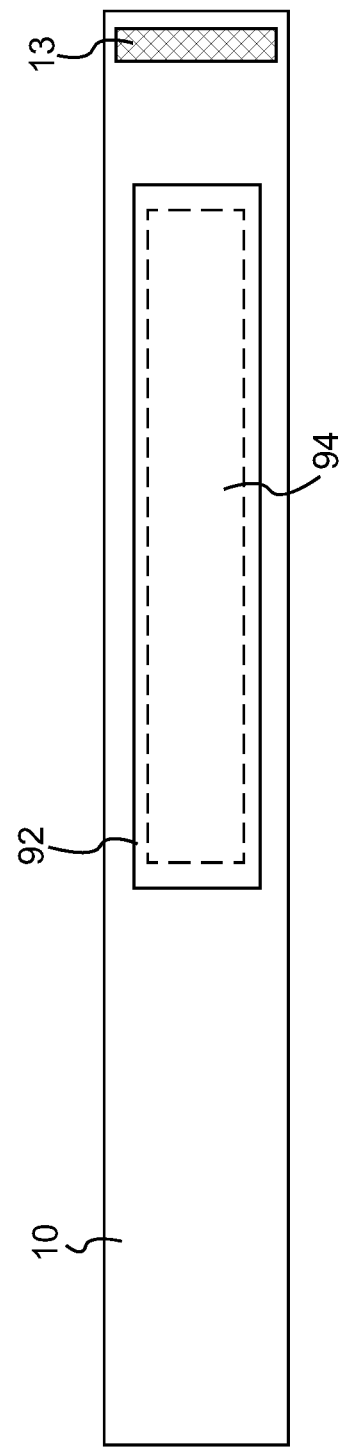
FIG. 19 is a schematic view of the endoscopy band device described in FIG. 18, with a rectangular heating pad inserted into the pouch, in accordance with aspects of the present invention.
Figure 20:
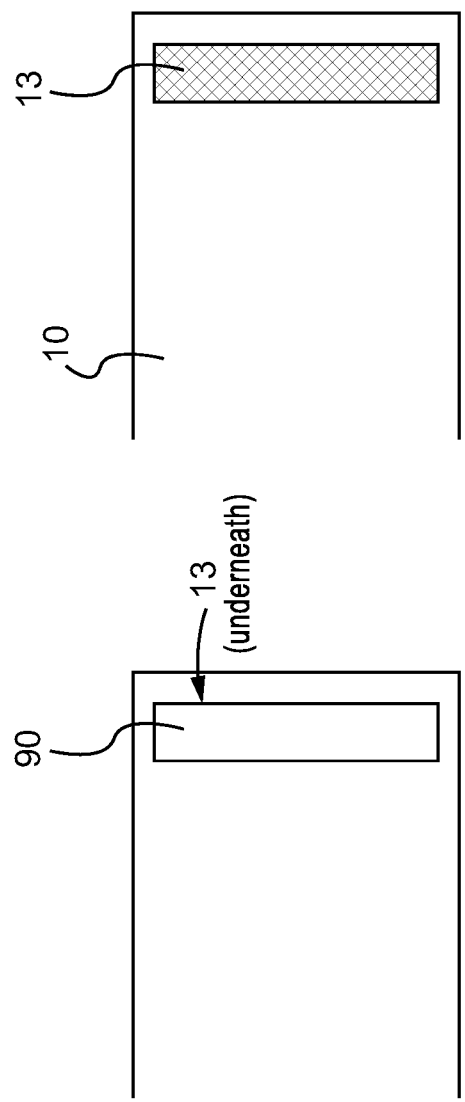
FIG. 20 is a schematic view of a disposable, removable cover for the hook strip on the inside of the primary wrap, in accordance with aspects of the present invention. The depiction on the left shows the cover applied to the hook strip, and the depiction on the right shows the cover removed in preparation for use.
Figure 26:
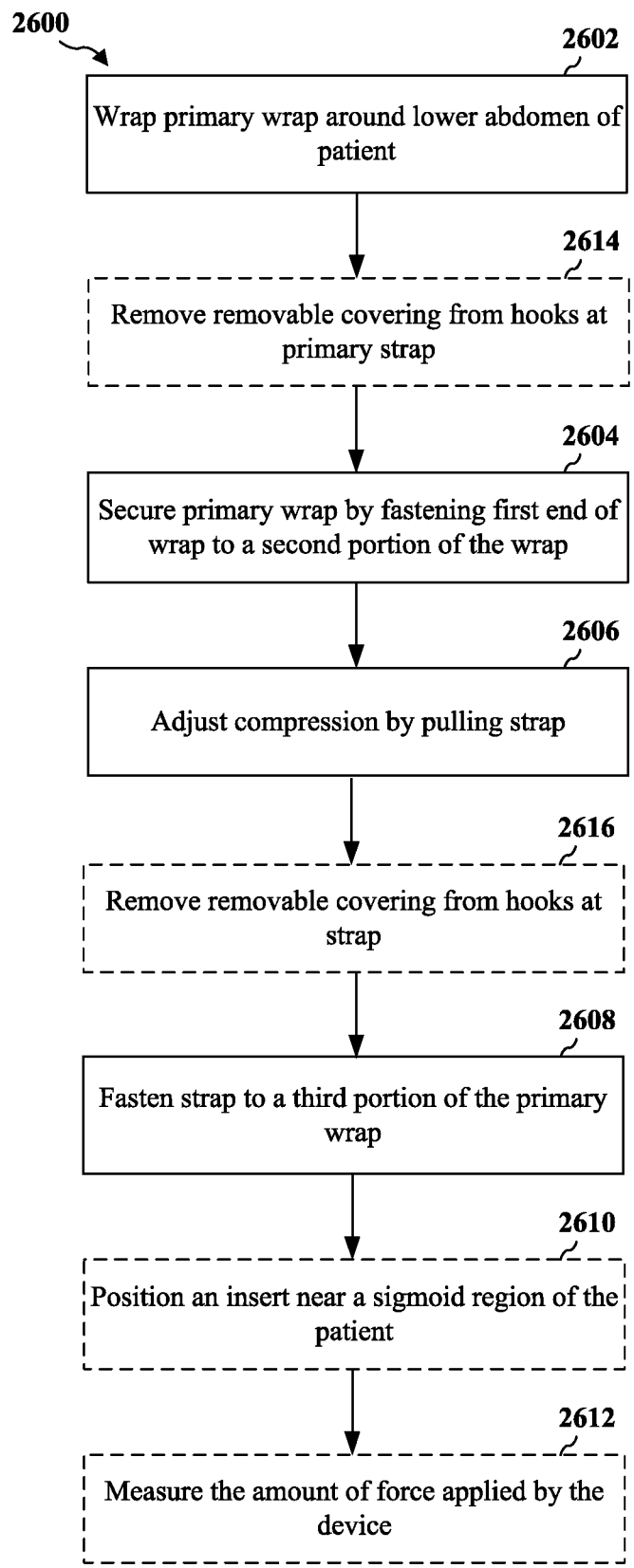
FIG. 26 illustrates aspects of a method for applying pressure and support to a patient's abdomen during advancement of an endoscope during an endoscopy type procedure, in accordance with aspects of the present invention.

Patients often become cold or uncomfortably chilled once they change into the garments such as hospital gowns typically worn while undergoing an endoscopic procedure. Many patients request and are provided with blankets, and some facilities provide electric heated blankets, or blankets that have been previously warmed. The heated blankets provide physical warmth, but also they tend to relax the patient and relieve anxiety or discomfort the patient may be experiencing. Aspects presented herein may also help the patient feel warm and comfortable. In FIGS. 18-19, e.g., a primary wrap 10 may be equipped with a pouch 92 that is attached or fastened to the interior side of the primary wrap 10. This pouch 92 may be capable of accepting and holding in place re-usable or disposable heating apparatuses, including the rectangular heating pad 94 shown in FIG. 19. FIG. 26 illustrates aspects of a method for applying pressure and support to a patient's abdomen during advancement of an endoscope during an endoscopy type procedure. At 2602, a primary wrap is wrapped around the lower abdomen of a patient, e.g., approximately between the hips and umbilicus of the patient.

After wrapping the primary wrap about the abdomen of the patient, the primary wrap is secured by attaching a first end of the primary wrap to a second portion of the primary wrap at 2604.

The amount of compression applied to the abdomen of the patient may be adjusted by pulling a strap extending from the primary wrap across at least a portion of the primary wrap at 2606 and fastening the strap to a third portion of the primary wrap at 2608. The strap may be coupled to a portion of the primary wrap that is configured for placement over a left side of the subject's lower abdomen. This allows the patient's own body weight to be leveraged in order to adjust the compression provided by the strap. The strap may be configured to be pulled in a direction toward a right side of the subject's lower abdomen to adjust the amount of pressure applied by the endoscopy sigmoid support apparatus.

Optionally, an insert may be positioned near a sigmoid region of the patient at 2610. This may involve placing the insert between the abdomen of the patient and the wrap and/or the strap. The insert may be configured to increase the compression applied to the sigmoid region, e.g., as described in connection with FIGS. 4, 5, and 8-11. In one example, the insert may be inserted into a receptacle formed in the primary wrap and/or the strap.

As another option, the primary wrap may comprise an insert, and the insert may be positioned over a lower left quadrant of the patient's abdomen over the sigmoid region prior to securing the primary wrap and adjusting the compression applied to the abdomen. A portion of the wrap and/or the strap may extend over the insert in order to adjust the compression applied by the insert.

As another option at 2612, the amount of force being applied by the endoscopy sigmoid support apparatus may be measured using a compression indicator. Among others, the indicator may comprise a gauge for measuring and indicating the amount of pressure applied to the abdomen of the subject and/or a visual indicator. For example, a strip of material may be used having at least one transparent window through which a mark or a set of marks can be viewed in order to determine the amount of pressure being applied. In another example, a visual mark may be provided directly on an elastic portion of the apparatus, and the deformation of the visual mark may be used to determine an amount of pressure being applied. An example deformed mark may be provided so that an operator can compare the example deformed mark to the deformation of the visual mark.

The primary wrap may comprise a first elastic portion and a second elastic portion separated by a relatively inelastic portion, and the method may include positioning the relatively inelastic portion over a sigmoid region of the subject's lower abdomen. One edge of the strap may be connected to the inelastic portion and a second edge may fasten to the primary wrap by extending the strap across the inelastic portion to increase compression at the inelastic portion. A second strap may be provided that extends from an attachment point on the primary wrap. For example, the second strap may be positioned on a side of the wrap opposite the strap. The second strap may be looped through a portion of the strap and pulled back toward the attachment point in order to adjust the compression applied to the subject.

The wrap and/or the strap may fasten using a hook and pile or hook and loop type fastening mechanism. A removable covering may be placed over the hook portion. Thus, at 2614 or 2616, the removable covering may be removed after the device is placed around the patient and prior to securing either the primary wrap or the strap.

Aspects may further include inserting a heating pad, e.g., into a receptacle within the primary wrap and/or strap.

To additionally enhance patient comfort, certain aspects of the invention are designed to be single-use, and to remain fastened in place on the patient following the procedure. This method of application may be used to reduce the common post-procedure complications of bloating and abdominal pain caused by bloating. Otherwise known as gaseous distention, bloating occurs following endoscopy procedures because physicians often use compressed air or carbon dioxide to insufflate parts of the bowel that are difficult to see and examine. The gas opens up the area to allow for a more complete visualization, enhancing the efficacy of the procedure. However, the gas also remains in the patient until it is either absorbed or expelled. Expulsion is the primary gas removal mechanism as absorption is a very inefficient process. Gaseous distention is a primary post-procedure complication and a frequent complaint from patients. However when the wrap described herein remains in place after the procedure, the lower abdominal compression generated by the device allows the bowel to more rapidly evacuate trapped by directing excess gas towards the rectum. As a result, the severity and duration of post-procedure bloating and associated abdominal pain may be reduced.

Example aspects of the present invention have now been described in accordance with the above advantages. It will be appreciated that these examples are merely illustrative of aspects of the present invention. Many variations and modifications will be apparent to those skilled in the art.

It is understood that the specific order or hierarchy of steps in the processes disclosed is an illustration of exemplary approaches. Based upon design preferences, it is understood that the specific order or hierarchy of steps in the processes may be rearranged. Further, some steps may be combined or omitted. The accompanying method claims present elements of the various steps in a sample order, and are not meant to be limited to the specific order or hierarchy presented.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." The word "exemplary" is used herein to mean "serving as an example, instance, or illustration." Any aspect described herein as "exemplary" is not necessarily to be construed as preferred or advantageous over other aspects." Unless specifically stated otherwise, the term "some" refers to one or more. Combinations such as "at least one of A, B, or C," "at least one of A, B, and C," and "A, B, C, or any combination thereof" include any combination of A, B, and/or C, and may include multiples of A, multiples of B, or multiples of C. Specifically, combinations such as "at least one of A, B, or C," "at least one of A, B, and C," and "A, B, C, or any combination thereof" may be A only, B only, C only, A and B, A and C, B and C, or A and B and C, where any such combinations may contain one or more member or members of A, B, or C. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed as a means plus function unless the element is expressly recited using the phrase "means for."

The invention claimed is:

1. An endoscopy support apparatus, comprising:
   a primary elastic wrap comprising a band of elastic material sized for placement around a subject's lower abdomen and configured to apply a selected degree of constant pressure and support through contraction of the band of elastic material across the subject's lower abdomen in order to facilitate passage of an endoscope;
   a closing mechanism provided at an end of the primary elastic wrap to secure the primary elastic wrap around the subject's lower abdomen; and
   an elastic secondary strap having a first, terminal end fixed to the primary elastic wrap at a left portion of the primary elastic wrap and configured to stretch left to right across a front abdomen portion of the primary elastic wrap on an exterior side and to removably couple at a second, non-fixed end to the primary elastic wrap at a non-fixed position to exert additional location specific compression to the subject's lower abdomen, wherein an additional degree of compression through contraction is adjustable based on a position at which the second, non-fixed end of the elastic secondary strap is coupled to the primary elastic wrap, wherein the elastic secondary strap comprises a tapered shape that tapers along more than half of a length of the elastic secondary strap from the first, terminal end to the second, non-fixed end.

2. The endoscopy support apparatus of claim 1, wherein the elastic secondary strap comprises the tapered shape that tapers along an entire length of the elastic secondary strap from the first, terminal end to the second, non-fixed end.

3. The endoscopy support apparatus of claim 1, further comprising:
   at least one looped handle positioned at the end of the primary elastic wrap separately from the elastic secondary strap and configured to assist in securing the primary elastic wrap around the subject's lower abdomen.

4. The endoscopy support apparatus of claim 1, further comprising multiple elastic secondary straps.

5. The endoscopy support apparatus of claim 1, wherein the elastic secondary strap comprises:

a hook type fastening material configured to removably couple to the primary elastic wrap at any point along the exterior side of the primary elastic wrap.

6. The endoscopy support apparatus of claim 5, wherein the hook type fastening material is configured to removably couple to the primary elastic wrap using a hook and pile type attachment.

7. The endoscopy support apparatus of claim 5, further comprising:
a removable covering applied over the hook type fastening material.

8. The endoscopy support apparatus of claim 1, wherein the elastic secondary strap comprises two fixed portions coupled to the primary elastic wrap along a vertical line, and wherein the second, non-fixed end includes a handle and a fastening mechanism at a midpoint that allows the elastic secondary strap to removably couple to the primary elastic wrap.

9. The endoscopy support apparatus of claim 1, further comprising:
an insert positionable between the subject and at least one selected from a group consisting of the primary elastic wrap and the elastic secondary strap,
wherein the insert is configured to provide directed compression on a region of the subject's lower abdomen.

10. The endoscopy support apparatus of claim 9, further comprising:
a receptacle formed on the primary elastic wrap for receiving the insert.

11. The endoscopy support apparatus of claim 9, wherein the insert is attached to the primary elastic wrap.

12. The endoscopy support apparatus of claim 9, wherein the insert comprises at least one of a tapered shape or a rounded shape.

13. The endoscopy support apparatus of claim 9, wherein the insert is sized to provide the compression on an area surrounding a sigmoid colon of the subject without engaging anatomical features that impede the compression of the sigmoid colon.

14. The endoscopy support apparatus of claim 9, wherein the primary elastic wrap comprises first elastic portion and a second elastic portion separated by a relatively inelastic portion, wherein the relatively inelastic portion is configured to be positioned over a sigmoid region of the subject's lower abdomen, and wherein the elastic secondary strap is configured to extend across the relatively inelastic portion.

15. The endoscopy support apparatus of claim 1, further comprising:
a visual mark indicator that indicates an amount of force being applied by the endoscopy support apparatus using a visual mark provided on the primary elastic wrap or the elastic secondary strap of the endoscopy support apparatus.

16. The endoscopy support apparatus of claim 15, wherein the visual mark indicator comprises a strip of material having at least one transparent window, wherein the visual mark can be viewed through the at least one transparent window to determine the amount of force being applied.

17. The endoscopy support apparatus of claim 15, wherein the visual mark indicator comprises an image or a printed word provided on an elastic portion of the endoscopy support apparatus, wherein a deformation of the image or the printed word is used to determine the amount of force being applied.

18. The endoscopy support apparatus of claim 1, further comprising a feature configured to visually indicate prior use.

19. The endoscopy support apparatus of claim 1, further comprising:
a receptacle for receiving a heating pad.

20. The endoscopy support apparatus of claim 1, wherein the elastic secondary strap includes two fixed ends that are fixed to the primary elastic wrap, and the second, non-fixed end comprises a midpoint between the fixed ends, wherein the two fixed ends are spaced to provide the tapered shape to the midpoint at the second, non-fixed end.

* * * * *